United States Patent [19]

MacFarlane et al.

[11] Patent Number: 5,209,933
[45] Date of Patent: May 11, 1993

[54] LONG ACTING CALCIUM CHANNEL BLOCKER COMPOSITION

[75] Inventors: Calum B. MacFarlane, Linlitchgow; Alastair B. Selkirk; John R. Langridge, both of Edinburgh; Michael J. Dey, East Calder, all of Scotland

[73] Assignee: Syntex (U.S.A.) Inc., Palo Alto, Calif.

[21] Appl. No.: 759,792

[22] Filed: Sep. 13, 1991

Related U.S. Application Data

[63] Continuation of Ser. No. 463,103, Jan. 10, 1990, abandoned.

[51] Int. Cl.$^5$ ................................................ A61K 9/16
[52] U.S. Cl. .................................... 424/494; 424/490; 424/497; 514/356
[58] Field of Search .................. 424/494, 490, 497; 514/356

[56] References Cited

U.S. PATENT DOCUMENTS

| | | | |
|---|---|---|---|
| 4,343,789 | 8/1982 | Kawata et al. | 428/78 |
| 4,665,100 | 5/1987 | Ludwig | 514/77 |
| 4,704,295 | 11/1987 | Porter | 424/497 |
| 4,758,437 | 7/1988 | Sonobe | 424/471 |
| 4,765,990 | 8/1988 | Sugimoto et al. | 424/494 |
| 4,816,264 | 3/1989 | Phillips | 424/497 |
| 4,857,312 | 8/1989 | Hegasy | 424/80 |
| 4,859,665 | 8/1989 | Garthoff | 514/221 |
| 4,940,556 | 7/1990 | MacFarlane | 264/15 |
| 4,970,081 | 11/1990 | Frisbee | 424/497 |

FOREIGN PATENT DOCUMENTS

0267386 9/1987 European Pat. Off. .

*Primary Examiner*—Thurman K. Page
*Assistant Examiner*—D. Gabrielle Phelan
*Attorney, Agent, or Firm*—David A. Lowin; Tom M. Moran

[57] ABSTRACT

There is disclosed an improved long acting sustained release pharmaceutical composition for dihydropyridine calcium channel blockers wherein the calcium channel blocker and a pH-dependent binder, which are intimately admixed in essentially spherically shaped non-rugose particles of up to 1.2 mm in diameter, are provided with a coating to obtain slow, sustained release of a safe, therapeutically effective amount of the calcium channel blocker over a period of at least about 24 hours. Thus, the improved pharmaceutical composition for a dihydropyridine calcium channel blockers is suitable for once daily administration.

8 Claims, 2 Drawing Sheets

LONG ACTING CALCIUM CHANNEL BLOCKER COMPOSITION

This is a continuation of pending application Ser. No. 07/463,103, filed Jan. 10, 1990, now abandoned, incorporated herein by reference.

BACKGROUND OF THE INVENTION

1. Field of the Invention

This invention concerns an improved long acting sustained release pharmaceutical composition and dosage form for dihydropyridine calcium channel blockers.

2. Description of Related References

Calcium channel blockers are a relatively recently discovered class of compounds which possess a wide spectrum of properties useful in the treatment of cardiovascular and cerebrovascular disorders. Among the clinical applications for which this class of compounds has shown some useful therapeutic properties are the treatment of classic exertional angina, vasospastic angina, angina pectoris, acute myocardial infarction, cardiac arrhythmias, systemic arterial hypertension, pulmonary arterial hypertension, and cardiomyopathies.

Several structural classes of compounds are known which exhibit calcium channel blocking utility. Compounds representative of some of these classes include nicardipine, verapamil, diltiazem, perhexiline and lidoflazine.

The structural class of calcium channel blockers of interest in this invention, of which nicardipine is a member, are 1,4-dihydropyridine-3,5-dicarboxylic acid derivatives of the general formula A:

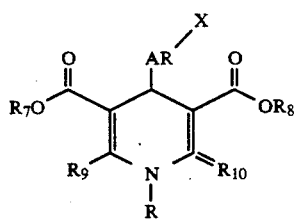

(A)

in which AR is a simple or fused aryl or heteroaryl ring moiety; X is hydrogen or one or more substituents on the AR moiety; $R_7$ and $R_8$ are independently hydrogen or ester forming moieties; $R_9$ and $R_{10}$ are independently methyl or various other 2 and 6 position substituents on the dihydropyridine ring, and R is hydrogen or an alkyl or simple aryl group. Examples of AR groups include, but are not limited to phenyl, pyridinyl, benzofurazanyl, benzoxadiazolyl and the like. Examples of X groups include, but are not limited to alkyl, halo, haloalkyl, alkoxy, haloalkoxy, alkoxycarbonyl, alkenyl, methylenedioxy, ethylenedioxy, nitro, cyano and the like. Examples of $R_7$ and $R_8$ ester forming moieties include, but are not limited to alkyl, alkoxy, haloalkyl, nitro, hydroxyalkyl, alkylenyloxyalkyl, phenylaminoalkyl, alkylaminoalkyl or alkoxyaminoalkyl, amino(carbonyl)oxyalkyl, or an optionally substituted simple or fused aryl, aralkyl or arylsulfonyl group such as, but not limited to, phenyl, phenylalkyl, phenylsulfonyl, phenylalkenyl, naphthyl, naphthylalkyl, dioxaphosphorinanyl, piperidinyl, pyrrolidinyl, furyl, pyrrolyl, pyridyl, imidazolyl, thienyl, morpholinyl, [(tetrahydropyran-2-yloxy)-alkyl]phenoxyalkyl or [(tetrahydropyran-2-yloxy)-alkyl]phenylthioalkyl. Examples of $R_9$ and $R_{10}$ substituents include, but are not limited to alkyl such as methyl, a substituted alkyl group such as hydroxyalkyl or aminoalkoxyalkyl, cyano, or optionally substituted phenylcarbonylalkyl; Examples of R groups other than hydrogen include, but are not limited to alkyl, benzyl, morpholinyl and morpholinylalkyl.

Many compounds within the general class represented by formula A are known and have been shown to have calcium channel blocking activity. It is known, for example, that 4-(2'-nitrophenyl)-2,6-dimethyl-1,4-dihydropyridine-3,5-dicarboxylic acid dimethyl ester shows calcium channel blocking activity (U.S. Pat. No. 3,644,627). Other compounds within this structural and pharmacologic class include those disclosed in U.S. Pat. No. 3,511,837 (4-pyrimidyl-1,4-dihydropyridine derivatives), U.S. Pat. No. 3,691,177 (cyanophenyl-1,4-dihydropyridine derivatives), German Offlegungsschrift No. 1,813,436 (N-alkyl-1,4-dihydropyridine derivatives), No. 1,963,185 (4-nitro and other group substituted phenyl-1,4-dihydropyridine derivatives), No. 1,963,186 (sulfur containing 4-aryl-1,4-dihydropyridine derivatives), No. 2,005,116 (1,4-dihydropyridine-3,5-dicarboxylic acid unsaturated alkyl esters), No. 2,3,146 (3-alkanoyl-1,4-dihydropyridine-5-carboxylic acid esters, U.S. Pat. No. 3,511,837 (1,4-dihydro-2,6-dimethyl-4-(2'-trifluoromethylphenyl)-3,5-pyridine dicarboxylic acid diethyl ester) and in BE 862-107, U.S. Pat. No. 4,017,629, DE 2,616,995, and German Offenlegungsschrift 3,501,695 (various 3-arylsulfonyl 1,4-dihydropyridine derivatives). Other 1,4-dihydropyridine compounds with cardiovascular activity are disclosed in U.S. Pat. Nos. 3,644,627 and 3,485,847, in German Offenlegungsschrift 1,670,827 and in Bundesrepublik Deutschland Auslegeschrift 17,92,764.

Specific compounds of formula A which can be incorporated in the long acting sustained release composition of this invention include 2,6-dimethyl-3-carbomethoxy-4-(3-nitrophenyl)-5-[3-(4-[2-(tetrahydropyran-2-yloxy)ethyl]phenoxy)propoxy carbonyl]-1,4-dihydropyridine disclosed in U.S. application Ser. No. 874,264 filed Jun. 13, 1986, now U.S. Pat. No. 4,761,420 issued Aug. 2, 1988, the disclosure of which is incorporated by reference herein; 3,5-pyridinedicarboxylic acid, 2-[(2-aminoethoxy)methyl]-4-(2-chlorophnyl)-1,4-dihydro-6-methyl, 3-ethyl 5-methyl ester, (±)-, (Z)-2-butenedioate, generic name: amlodipine; 3,5-pyridinedicarboxylic acid 4-(4-benzofurazanyl)-1,4-dihydro-2,6-dimethyl-, diethyl ester, generic name: darodipine; 3,5-pyridinedicarboxylic acid, 1,4-dihydro-2,6-dimethyl-1-[2-(4-morpholinyl)ethyl]-4-[2-(trifluoromethyl)phenyl]-, diethyl ester, generic name: flordipine; 1,4-dihydro-2,6-dimethyl-4-(2-trifluoromethylphenyl)-3,5-pyridinedicarboxylic acid 2-([1-(4-hydroxyphenyl)-3-oxopropyl]amino)ethyl ester), generic name: iodipine; isopropyl methyl 4-(4-benzofurazanyl)-1,4-dihydro-2,6-dimethyl-3,5-pyridine dicarboxylate, generic name: isodipine; diethyl 1',4'-dihydro-2',6'-dimethyl-2-(methylthio)[3,4'bipyridine]-3'5'-dicarboxylate, generic name: mesudipine; 3,5 pyridinedicarboxylc acid, 2-cyano-1,4-dihydro-6-methyl-4-(3-nitrophenyl)-, 3-methyl 5-(1-methylethyl) ester, generic name; nilvadipine; ethyl methyl 1,4-dihydro-2,6-dimethyl-4-[2,3-(methylenedioxy)-phenyl-3,5-pyridinedicarboxylate, generic name: oxodipine; dimethyl 4-[o-(di-fluoromethyl)-phenyl]-1,4-dihydro-2,6-dimethyl-3,5-pyridine dicarboxylate, generic name: riodipine; methyl 2,6-dimethyl-4-(2-nitrophenyl)-5-(2-oxo-1,3,2-dioxaphosphorinan-2-yl)-1,4-dihydropyridine 3-carboxylate; 1,4-dihydro-2- hydroxmethyl-4-(m-nitrophenyl)-6-methyl-3,5-pyridine dicarboxylic acid diethyl ester; methyl (E)-3-phenyl-2-propeny-1-yl-1,4-dihydro-2,6-dimethyl-4-(3-nitrophenyl)pyridine-3,5-dicarboxylate; (E)-4-(2-(3-(1,1-dimethylethoxy)-3-oxo-1-propenyl)phenyl-1,4-dihydro-2,6-dimethyl-3,5-pyridinedicarboxylic acid, diethyl ester; 1,4-dihydro-2,6-dimethyl-4-(3-nitrophenyl)-3,5-pyridinedicarboxylic acid methyl 1-(phenylmethyl)-3-piperidinyl ester monohydrochloride; 3-(2-furoyl)-5-methoxycarbonyl-2,6-dimethyl-4-(2-nitrophenyl)-1,4-dihydropyridine; 3,5-pyridinedicarboxylic acid 2-(((aminocarbonyl)oxy)methyl)-4-(2,3-dichlorophenyl)-1,4-dihydro-6-methyl-5-methyl 3-(1-methylethyl)ester; 1-benzyl-3-pyrrolidinyl methyl 2,6-dimethyl-4-(m-nitrophenyl)-1,4-dihydropyridine-3,5-dicarboxylate; and isopropyl 4-(2,1,3-benzoxadiazol-4-yl)-1,4-dihydro-2,6-dimethyl-5-nitro-3-pyridinecarboxylate.

Calcium channel blockers of particular interest in this invention are compounds selected from the group represented by the formula:

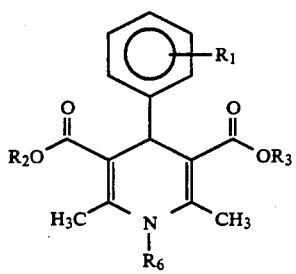

(I)

where;

$R_1$ is —$NO_2$, —$CF_3$, or halo;

$R_2$ is alkyl or —$CH_2CH_2OCH_3$; and $R_6$ is hydrogen or alkyl; and $R_3$ is alkyl, alkylenyloxyalkyl, haloalkyl, optionally substituted phenyl alkyl, optionally substituted napthyl alkyl, or

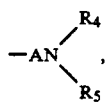

in which:

A is alkylene;

$R_4$ is alkyl, alkoxy, or optionally substituted phenyl or phenyl alkyl; and $R_5$ is hydrogen or alkyl;

and the pharmaceutically acceptable salts thereof.

Several compounds within this group are known to possess a high degree of calcium channel blocking activity. These include, for example, 4-(2'-nitrophenyl)-2,6-dimethyl-1,4-dihydropyridine-3,5-dicarboxylic acid dimethyl ester, generic name: nifedipine (U.S. Pat. No. 3,644,627); 4-(3'-nitrophenyl)-2,6-dimethyl-1,4-dihydropyridine-3,5-dicarboxylic acid di-n-propyloxethyl ester, generic name: niludipine; 4-(3'-nitrophenyl)-2,6-dimethyl-1,4-dihydropyridine-3,5-dicarboxylic acid 3-ethyl ester 5-methyl ester, generic name: nitrendipine; 4-(3'-nitrophenyl)-2,6-dimethyl-1,4-dihydropyridine-3,5-dicarboxylic acid 3-methyl ester 5-(2-methoxyethyl)ester, generic name: nimodipine; 4-(2'-nitrophenyl)-2,6-dimethyl-1,4-dihydropyridine-3,5-dicarboxylic acid 3-methyl ester 5-isobutyl ester, generic name: nisoldipine; 4-(2',3'-dichloro)-2,6-dimethyl-1,4-dihydropyridine-3,5-dicarboxylic acid 3-ethyl ester 5-methyl ester, generic name: felodipine; 4-(3'-nitrophenyl)-2,6-dimethyl-1,4-dihydropyridine-3,5-dicarboxylic acid 3-methyl ester 5-$\beta$-(N-benzyl-N-methylamino)-ethyl ester, generic name: nicardipine; isopropyl methyl 1,4-dihydro-2,6-dimethyl 4-(3-nitrophenyl)-3,5-pyridine dicarboxylate; and 2,6-dimethyl-3,5-diethoxycarbonyl-4-(o-difluoromethylphenyl)-1,4-dichydropyridine.

Other compounds of Formula I which can be practically administered from the long acting sustained release compositions of this invention include 2,6-dimethyl-3,5-bis(methoxycarbonyl)-4-phenyl-1,4-dihydropyridine, 2,6-dimethyl-3,5-bis(methoxycarbonyl)-4-(3-methylphenyl)-1,4-dihydropyridine, 2,6-dimethyl-3,5-bis(methoxycarbonyl)-4-(3-cyanophenyl)-1,4-dihydropyridine, 2,6-dimethyl-3,5-bis(methoxycarbonyl)-4-(3-nitrophenyl)-1,4-dihydropyridine, 2,6-dimethyl-3,5-bis(methoxycarbonyl)-4-(4-nitrophenyl)-1,4-dihydropyridine, 2,6-dimethyl-3,5-bis(methoxycarbonyl)-4-(4-methylphenyl)-1,4-dihydropyridine, 2,6-dimethyl-3,5-bis(methoxycarbonyl)-4-[4-(dimethylamino)-phenyl]-1,4-dihydropyridine, 2,6-dimethyl-4-phenyl-1,4-dihydropyridine 3,5-dicarboxylacid diethyl ester, 2,6-dimethyl-3,5-bis(methoxycarbonyl)-4-(2,4-dinitrophenyl)-1,4-dihydropyridine, 2,6-dimethyl-3,5-bis(methoxycarbonyl)-4-[2-(trifluoromethyl)phenyl]-1,4-dihydropyridine, and 2,6-dimethyl-3,5-bis(methoxycarbonyl)-4-(pentafluorophenyl)-1,4-dihydropyridine, all of which are disclosed in J. Med. Chem (1986) 29 (12), pp. 2504–2511.

Calcium channel blockers of the 1,4-dihydropyridine class share a number of pharmacological and pharmacokinetic properties in common which render them well suited to administration by the long acting sustained release methods of this invention. They are drugs which are extensively lipid-soluble and therefore are widely and extensively distributed within body tissues at steady state. They are also rapidly absorbed after oral administration, showing peak plasma levels within approximately about one hour ($T_{max}$). The half-life of elimination of these compounds is generally in the range of two to five hours, thus necessitating administration of standard oral dosage forms three to four times daily.

Additionally, some of the compounds, in particular, nicardipine, undergo extensive first pass metabolism.

The pharmaceutical compositions and dosage forms of this invention are particularly well suited for the administration of nicardipine and its pharmaceutically acceptable salts, such as nicardipine and hydrochloride. The preparation and use of nicardipine and other closely related compounds and their pharmaceutically acceptable salts are described in U.S. Pat. No. 3,985,758, the disclosure of which is incorporated by reference herein.

At the present time, the preferred route of administration for most therapeutic applications of the dihydropyridine calcium channel blockers is via an oral dosage form. These are typically compressed tablets, hard gelatin capsules filled with a powder mix, or soft gelatin capsule filled with a solution, and are conventionally administered three or four times daily.

However, conventional release oral dosage forms are poorly suited to dihydropyridine calcium channel blocker therapy. At the low pH that often occurs in the stomach, the solubility of the basic dihydropyridines is relatively high, resulting in rapid dissolution and absorption. At higher gastro-intestinal pH values, dihydropyridine solubility, and hence the dissolution rate, decreases. As a result, conventional release oral dosage forms release calcium channel blocker more rapidly in the more acidic regions and less rapidly in the less acidic regions of the gastrointestinal tract. The release profiles of such dosage forms are inherently dependent upon the local pH.

There is a need, therefore, for a long acting dosage form with sustained release properties capable of providing therapeutic calcium channel blocker plasma concentrations when the dosage form is administered less frequently, preferably once or twice daily. In addition to providing convenience for the patient, such a sustained release dosage form would minimize undesirable fluctuations in drug plasma concentration.

In Kawata et al., U.S. Pat. No. 4,343,789, formulations and dosage forms for nicardipine and related compounds are described which provide some dissolution control, and hence sustained release of the drug. As described in the patent, there is formed a powder containing amorphous nicardipine, polyethylene oxide, and other excipients which can then be formed into granules, tablets, pills or capsules by conventional means. The formulation requires that the nicardipine or salt thereof be in amorphous form, and be combined with polyethylene oxide in a fine particle powder or granules. The formulation may additionally contain a pH-dependent agent for dissolution control, such as a copolymer of methacrylic acid and a methacrylic acid ester. While the specific disclosure is primarily directed to tablet formulations, one capsule dosage form is disclosed (in Example 9) which contains small coated pills obtained by film coating a mixed powder containing nicardipine hydrochloride with a solution of methyl cellulose in water, and then further coating part of the coated pills with an organic solution of Eudragit (methacrylic acid/methyacrylic acid ester copolymer).

However, the preparation of the drug in amorphous form and the incorporation of polyoxyethylene are time consuming and expensive manufacturing procedures. Other granular and particulate calcium channel blocker compositions formulated with a pH-dependent binding agent are known. However, the manufacture of these compositions has required the use of an organic solvent, which must subsequently be removed by arduous and lengthy drying procedures and always leaving the risk of toxic residues.

Ludwig, U.S. Pat. No. 4,665,100, discloses a method of formulating a synthetic drug for use in a feed which will reduce the carryover of the drug from one lot of feed to a subsequent lot in feed mill operations. The patented process involves intimately mixing the drug (about 1-40% of minigranule on a dry weight basis) with a carrier (50-98% on a dry weight basis), a physiologically acceptable binder (about 1-10% on a dry weight basis), and water, extruding the mixture through a perforated plate having relatively small apertures (about 0.5-1.5 mm) into elongated strands of extrudate, and contacting the elongated strands of extrudate with a moving frictional plate, imparting motion to said extrudate and developing a tumbling, rolling bed thereof wherein the strands are reduced to nearly spherical particals, called minigranules, drying them to remove excess moisture, and seiving the minigranules through meshed wire screens to obtain desired particle size.

Sugimoto et al., U.S. Pat. No. 4,765,990 (Aug. 23, 1988), disclose a sustained-release preparation containing nifedipine which comprises a Composition A and Composition B in a ratio of 15:85 to 50:50 by weight of nifedipine. Composition A is a rapid-release preparation containing as an active ingredient nifedipine fine powder of not more than 5 microns. Composition B is a delayed-release preparation containing as the active ingredient nifedipine fine powder having an average particle size of not more than 5 microns and having a surface coating layer comprising a non-toxic, hardly water-soluble substance and an enteric high molecular compound.

EP 0,267,386 (Derwent Abstract 88-134312/20) discloses solid, sustained release nifefipine dosage forms comprising, nifedipine and low-viscosity ethyl cellulose on a carrier comprising a hydroxyalkyl cellulose, a sugar and starch.

There is disclosed in U.S. Ser. No. 057,469 filed Jul. 26, 1987, now U.S. Pat. No. 4,940,596, owned in common by the assignee of this application for patent, a composition which was conceived for the purpose to overcome some of what were perceived as disadvantages or deficiencies of the references mentioned above, particularly with respect to Kawata et al., U.S. Pat. No. 4,343,789. The composition of the above-mentioned patent application comprises essentially spherical, non-coated, non-rugose particles having diameters up to 1.2 mm, comprising an effective amount of a calcium channel blocker in intimate admixture with at least 3 weight percent of a pH-dependent binder which is less soluble at lower pH and more soluble at higher pH. This composition provides therapeutic plasma concentrations of calcium channel blocker suitable for twice daily administration of the pharmaceutical composition.

Although the pharmaceutical composition described in the preceding paragraph is quite useful and effective and represents an improvement over the art described in the foregoing passages, there remains a need for a pharmaceutical composition which (1) provides therapeutically effective dihydropyridine calcium channel blocker plasma levels when administered even less frequently than twice daily, (2) avoids the risk of the phenomenon of "dose dumping," which is essential at the higher doses given once daily (3) provides readily and economically manufacturable drug-containing particles of substantially uniform and regular size and shape suitable for incorporation in hard gelatin capsules and other oral and parenteral dosage forms and uses the thermodynamically stable powder form of the drug thereby avoiding the inherent physical stability and consequent changing bioavailability of a thermodynamically unstable amorphous form.

SUMMARY OF THE INVENTION

This invention is an improved long acting sustained release pharmaceutical composition for dihydropyridine calcium channel blockers wherein the calcium channel blocker and a pH-dependent binder, which are intimately admixed in essentially spherically shaped non-rugose particles of up to 1.2 mm in diameter, are provided with a coating to obtain slow, sustained release of a safe, therapeutically effective amount of the calcium channel blocker over a period of at least about 24 hours and to thereby provide for once daily administration.

DETAILED DESCRIPTION OF THE INVENTION

Figure 1:
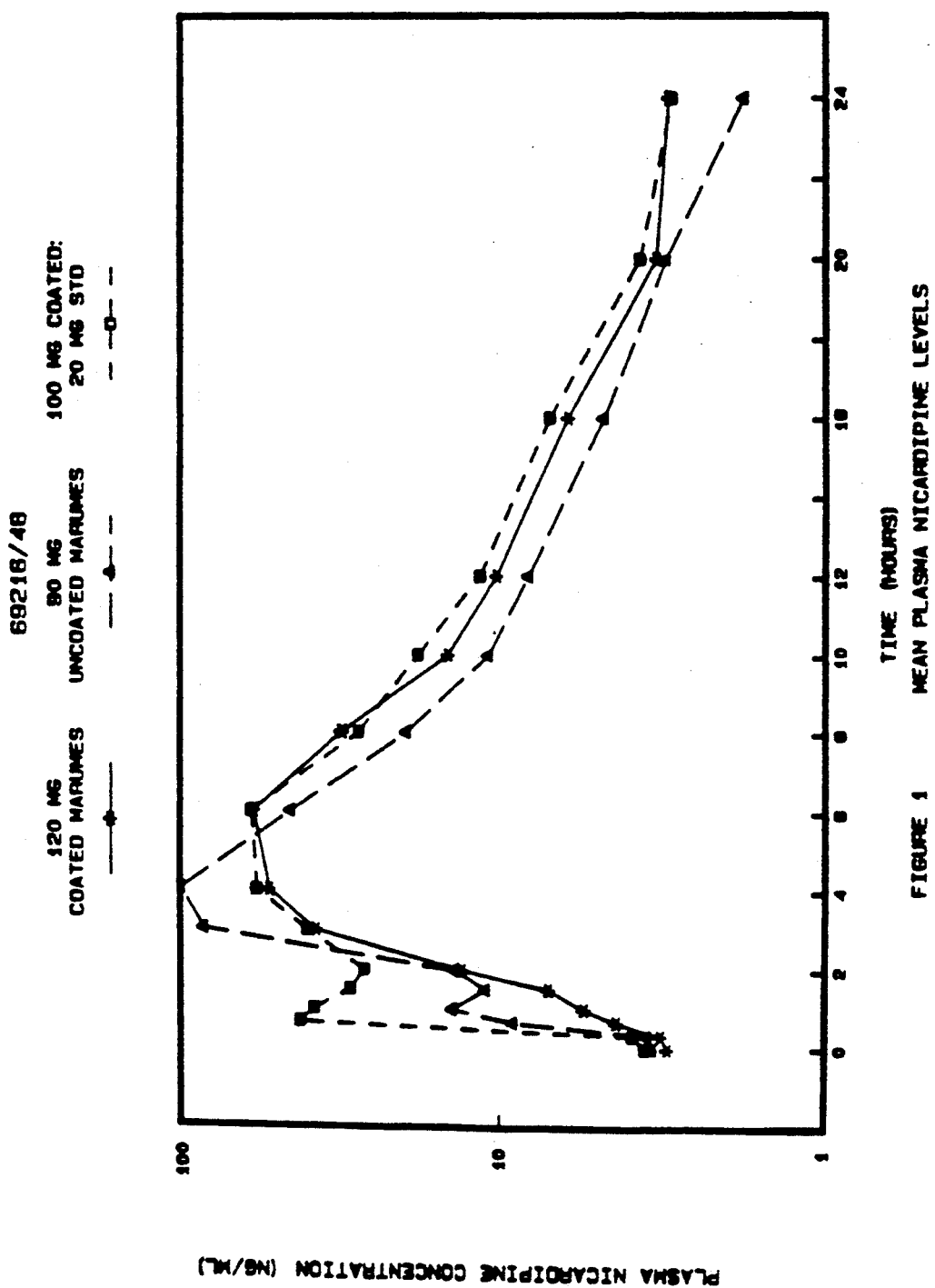
FIG. 1 is a graph showing nicardipine HCl levels in humans over a period of 24 hours for formulations comprising uncoated marumes (non-rugose spherical particles), coated marumes and coated marumes plus fast release powder.

More particularly, this invention is, in an improved long acting sustained release pharmaceutical composition for administration of a therapeutically effective amount of a dihydropyridine calcium channel blocking agent, useful in the treatment of disease conditions that may be alleviated by the administration of calcium channel blocking agents, which comprises essentially spherical, non-coated, non-rugose particles having diameters up to 1.2 mm, comprising a therapeutically effective amount of calcium channel blocking agent in intimate admixture with at least about 3 weight percent of a pH-dependent binder which is less soluble at lower pH and more soluble at higher pH:

the improvement comprising providing said composition with a coating to obtain slow, sustained release of a safe, therapeutically effective amount of the calcium channel blocking agent over a period of at least about 24 hours and to thereby provide for once daily administration.

DEFINITIONS

As used herein, the following terms have the meaning described below unless otherwise indicated:

The term "alkyl" refers to a straight or branched hydrocarbon chain having from one to six, preferably one to four carbon atoms. Examples of alkyl groups are methyl, ethyl, n-propyl, i-propyl, n-butyl, i-butyl, s-butyl and t-butyl.

The term "alkoxy" means a moiety of the formula —OR in which R is alkyl as defined above.

The term "alkylenyl" means a straight or branched chain bivalent alkyl bridging group.

The term "alkylenyloxyalkyl" means a moiety of the formula —R$_a$OR in which R$_a$ is alkylenyl and R is alkyl as defined above.

The term "halo" refers to chloro, bromo, iodo and fluoro. Nitro is a preferred halo substituent on the phenyl ring of the 1,4-dihydropyridyne calcium channel blockers compounds of interest in this invention.

The term "aryl" refers to homocyclic and heterocyclic moieties which are substantially aromatic in character. Examples of aryl groups are phenyl, naphthyl, imidazolyl, pyrrolyl, pyridinyl, thienyl, benzofurazanyl, benzoxadiazolyl and the like. The term "aralkyl" refers to a alkylaryl moieties.

The terms "phenyl alkyl" and "napthyl alkyl" mean radicals of the structure:

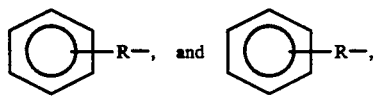

respectively, in which R is alkyl as defined above. In the case of the phenyl alkyl group, R may be in an.o-, m-or p-position. In the case of the napthyl alkyl group, R may be in the 5-, 6-, 7-, or 8-position.

Unless otherwise indicated or defined, a chemical substituent name which consists of compounded chemical group names is written in the order of appearance of the individually named groups starting with the terminus of the substituent. For example, "hydroxyalkyl" means a substituent of the formula —ROH where R is alkyl, and "alkoxyaminoalkyl" means a substituent group of the general formula —RNOR in which both R's are alkyl.

The terms "optional" and "optionally" mean that the subsequently described event or circumstance may or may not occur, and that the description includes instances where said event or circumstance occurs and instances in which it does not. For example, "optionally substituted phenyl" means that the phenyl moiety may or may not be substituted and that the description includes both substituted and unsubstituted phenyl. The phrase "optional pharmaceutical excipients" indicates that a composition or dosage form so described may or may not include pharmaceutical excipients other than those specifically stated to be present, and that the formulation or dosage form so described includes instances in which optional excipients are present and instances in which they are not.

The term "pharmaceutically acceptable acid addition salts" refers to salts of the subject compounds which possess the desired pharmacological activity and which are neither biologically nor otherwise undesirable. These salts are formed with inorganic acids such as hydrochloric acid, hydrobromic acid, sulfuric acid, nitric acid or phosphoric acid and the like; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

"Dihydropyridine calcium channel blocker" refers generally to any compound which contains the dihydropyridine dicarboxylic acid moiety and has calcium channel blocking activity. The compounds of formulas A and I described above in the Background of the Invention are representative of the dihydropyridine calcium channel blockers intended for use within the scope of this invention. Dihydropyridine calcium channel blockers not specifically described here may be beneficially administered from, and are included within the scope of, this invention.

"Nicardipine" identifies the compound 2,6-dimethyl-4-(3'-nitrophenyl)-1,4-dihydropyridine-3,5-dicarboxylic acid-3-β-(N-benzyl-N-methylamino)-ethyl ester 5-methyl ester, or any of its pharmaceutically acceptable salts. The salt, nicardipine hydrochloride, is the preferred calcium channel blocker of this invention.

The terms "treating" and "treatment" refer to any treatment of a disease in a mammal, particularly a human, and include: (i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The terms "fast release" and "conventional release" refer to calcium channel blocker composition that are substantially completely dissolved and absorbed in the stomach or upper gastrointestinal tract.

The terms "long acting" and "sustained release" refer to calcium channel blocker compositions that are slowly and continuously dissolved and absorbed in the stomach and gastrointestinal tract over a period of at least two hours. Preferred long acting compositions and dosage forms exhibit plasma concentration profiles suitable for once daily administration of the dosage form.

The pharmaceutical compositions, dosage forms and methods of the invention can be used to provide long acting sustained release administration of any of the 1,4-dihydropyridine derivatives having calcium channel blocking activity. The preferred dihydropyridine calcium channel blockers of this invention are selected from the group represented by the formula:

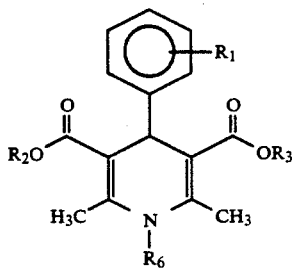

(1)

where;
$R_1$ is $-NO_2$, $-CF_3$, or halo;
$R_2$ is alkyl or $-CH_2CH_2OCH_3$; and
$R_6$ is hydrogen or alkyl; and
$R_3$ is alkyl, alkylenyloxyalkyl, haloalkyl, optionally substituted phenyl alkyl, optionally substituted napthyl alkyl, or

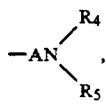

in which:
A is alkylene;
$R_4$ is alkyl, alkoxy, or optionally substituted phenyl or phenyl alkyl; and $R_5$ is hydrogen or alkyl;
and the pharmaceutically acceptable salts thereof.

The long acting sustained release pharmaceutical composition of the invention contains particles of calcium channel blocking agent which are coated spheroids, that is, essentially spherical particles having substantially smooth, non-rugose surfaces which are coated with a coating material, preferably a coating material which is poorly soluble at about pH 4.5 and below, but readily soluble at, about pH of 5.5 and above. In contrast to conventional granules, which may be approximately spherical in their outermost surface dimensions, but are actually loose particulate aggregates with highly rugose surfaces and area radius to circumference radius ratios in the range of 0.6 to 0.8, the spheroids used in the composition according to this invention have area radius to circumference radius ratios in the range of 0.85 to 1.0, preferably in the range of 0.9 to 1.0. As used herein area radius is given by the formula:

the square root of [the projected area divided by pi], and the circumference radius is given by the formula:

the projected circumference divided by 2 pi.

The projected area and projected circumference including indentations or projections are determined from a projected image of the particles in question. As used herein, "non-rugose" refers to an outer surface which is substantially lacking in wrinkles, craters and other surface irregularities. The terms "spheroids" and "spherical particles" are used interchangeably herein.

Further in contrast to conventional granules, the spheroids of this invention are relatively dense. Whereas conventional granules have variable and significant degrees of porosity in the range of about 30–50% internal void volume (see for example, Chalmers A. A. and Elworthy P. H. (1976) *J. Pharm. Pharmacol.*, 28, 239–243), the spheroids of this invention have substantially decreased porosities in the range of less than about 20% internal void volume, preferably 15% internal void volume or less. The smooth surface and low porosity of the spheroids provide substantially greater dissolution control than can be achieved with conventionally manufactured granules.

The spheroids and their preparation are disclosed and claimed in U.S. Ser. No. 057,469 filed Jul. 26, 1987, now U.S. Pat. No. 4,940,596 owned in common by the assignee of this application. Spheroids used in this invention are prepared from an essentially aqueous, wet mass containing the calcium channel blocker, pH-dependent binder, and any optional pharmaceutical excipients. The term "essentially aqueous, wet mass" refers to a powder mass which has been wetted with an essentially aqueous binding solution to a consistency suitable for extrusion. The powder mass is made by dry-blending the active ingredient(s) and any desired optional pharmaceutical excipients such as a diluent. The term "essentially aqueous" means that water is the predominant liquid in the binding solution, which may include, but preferably will not include, up to 25% other water-miscible solvents.

In the preferred embodiments of the spheroids, the pH-dependent binder may be dissolved or dispersed in the aqueous binding solution which is used to wet the dry powder mass or it may in some instances be preferable to include some or all of the pH-dependent binder in the dry powder mass prior to wetting with water or other essentially aqueous binding solution. Whether the pH-dependent binder is included in the dry powder mass or in the aqueous wetting solution, or both, the mixing of components which takes place to form and extrude the wet mass should be sufficient to place the active agent in intimate and substantially uniform admixture with the binder and any other excipients which may be incorporated.

In addition to, and intimately admixed with the calcium channel blocker and the pH-dependent binder in the wet mass may be other optional pharmaceutically acceptable excipients. These may include diluents such as lactose, mannitol, dry starch, microcrystalline cellulose and the like, additional binders such as starch, gelatin, sugars, carboxymethylcellulose, methylcellulose and the like, lubricants such as talc and magnesium stearate, neutralizing agents such as sodium hydroxide, potassium hydroxide and the like, surface active agents such as polyoxyethylene sorbitan esters, sorbitan esters and the like, coloring agents and flavoring agents.

The wet mass is then extruded to form rod-shaped, substantially cylindrical segments having diameters in the range of up to 1.2 millimeters. As used herein, the term "extrusion" refers to a process whereby a cohesive rod-shaped, substantially cylindrical material of specific cross section is formed by forcing the wet mass, from a wide diameter reservoir, through an orifice of small diameter, such that the product substantially retains the cross section of the orifice. These rod-shaped segments can then be formed into spheres, as described below, and it is therefore important that they be substantially cylindrical and of relatively uniform cross section. The extrusion step should also impart additional density (low porosity) to the material, which may be further densified during the spheronization step.

There are a wide variety of such extrusion methods known and available in the pharmaceutical industry. In general, these methods rely on generation of a continuous pressure of sufficient magnitude to induce the material to flow and retain the shape of the die on exit. The degree of wetness, flow and cohesive properties of the wet mass also affect the quality and uniformity of the extruded material. Well known, standard types of extrusion equipment suitable for use in this invention include screw extruders, cylinder extruders, gear extruders, ram extruders and radial screen rotating head type extruders.

The extruded rod-shaped segments are then shaped into spherical particles, which when dry and optionally coated, are long acting sustained release spheroids suitable for use in a variety of oral and parenteral dosage forms. As discussed above, in order to provide the desired prolonged dissolution and release profiles, the outer surface of the spheroids must be substantially smooth, non-rugose and essentially spherical. Spheronization equipment capable of forming spheroids having the desired properties from cylindrical extrudate is commercially available. For example, the Marumerizer machine (Conine J. W. and Hadley H. R., (1970) Drug Cosmet. Ind., 106, 38–41) can be used to provide spherical particles of suitable surface smoothness and regularity of size and shape. In the Marumerizer, the rod-shaped segments of extrudate are shaped into spheroids by centrifugal and frictional forces on a rotating disc or pan. This method of spheronization offers the opportunity to regulate the size of the spherical particles.

The dried, spherical granules may be film coated with a polymer in a variety of equipment such as an open rotating pan, a side vented rotating pan (e.g. Manesty Accelacota®), a fluidized bed coating column or a Wurster column. All of these machines provide a means of mixing and drying the spherical granules and at the same time applying a solution or suspension of the coating polymer in an organic, or preferably substantially aqueous, medium. The coated and dried spherical granules may optionally then be blended with an agent such as talc or colloidal silicon dioxide or the like to reduce static charges and facilitate subsequent handling.

The spheroids may be varied in size up to about 1.2 mm, and the size of the spheroids can be adjusted to control the rate of spheroid dissolution and drug release. Smaller spheroids have higher surface to volume ratios, and hence faster dissolution rates, than larger spheroids. The preferred size for spheroids is between about 0.5 mm and 1.2 mm, most preferably between about 0.7 mm and 1.0 mm. It is also preferred that the size distribution of the spheroids be as narrow as possible; spheroids within a narrow size distribution range provide a plasma concentration profile which is more flat and constant than that achieved with particles of widely differing sizes. In the preferred embodiments, at least 70 weight percent of the spheroids used in the compositions according to this invention will have diameters which are within upper and lower limits differing by not more than a factor of the square root of two from each other.

In order to provide sustained release of the dihydropyridine calcium channel blocker, the binder and coating materials suitable for use in the spheroids used in this invention must control the dissolution profile of the drug-containing spheroids so that they dissolve slowly and continuously throughout their passage within the stomach and along the gastrointestinal tract. The dissolution control capacity of the binding and coating agent is particularly important in a long-acting dosage form; a sustained release dosage form which contains sufficient drug for once or twice daily administration may cause untoward side effects if it dissolves too rapidly and dumps all of the drug into the gastrointestinal tract in a short period of time.

Accordingly, binders and coating materials suitable for use in the spheroids used in this invention are materials which prevent rapid dissolution of drug from the spheroids during their residence in those regions of the gastrointestinal tract where the pH is about 4.5 or less, and allow dissolution of the drug from the spheroids in the small and large intestines (where the pH is generally greater than about 5.5). Any material which is pharmaceutically acceptable for oral ingestion and which can impart such dissolution control to the calcium channel blocker spheroids can be used in this invention. Generally these materials are substantially insoluble at a pH of less than about 4.5 and are soluble at a pH of greater than about 5.5. Many materials known in the pharmaceutical art as "enteric" binders and coating agents have the desired properties. These include a large number of phthalic acid derivatives such as the phthalic acid derivatives of vinyl polymers and copolymers, hydroxyalkylcelluloses, alkylcelluloses, cellulose acetates, hydroxyalkylcellulose acetates, cellulose ethers, alkylcellulose acetates, and the partial esters thereof; and polymers and copolymers of lower alkyl acrylic acids and lower alkyl acrylates, and the partial esters thereof.

Examples of specific pH-dependent binder materials which may be used include hydroxypropyl cellulose phthalate, cellulose acetate phthalate, polyvinylacetate phthalate, polyvinylpyrrolidone phthalate, hydroxypropylmethyl cellulose phthalate and copolymers of methacrylic acid and methacrylic or acrylic acid esters. Particularly preferred binders for use in this invention are the commercially available copolymers of methacrylic acid and a methacrylic or acrylic acid ester, for example the Eudragit polymers, particularly the Eudragit L series such as Eudragit L30D and Eudragit L100/55, sold by the Rohm and Haas Company. Eudragit L100-55 and Eudragit L30D (a dispersion of 30% Eudragit L powder in water) are the preferred pH dependent binder and coating materials for use in this invention. It is to be noted that viscosity enhancing agents such as hydroxypropylmethylcellulose, methylcellulose and polyvinylpyrolidone which dissolve at a rate independent of pH, do not provide the required dissolution control.

The spheroids may contain the calcium channel blocker in any proportion from as little as 1 weight percent or less up to about 95 weight percent. The pH-dependent binder may be present in any proportion from as little as 3 weight percent up to about 95 weight percent. While the proportion of active agent present will depend largely on its potency, the proportion of pH-dependent binder will depend on the degree of release rate control which is needed for the particular active agent. Generally, the pH-dependent binder will constitute about 5 to 50 weight percent, preferably about 5 to 25 weight percent of each spherical particle. A preferred spheroid composition for the administration of nicardipine hydrochloride will contain about 40 to 50 weight percent nicardipine hydrochloride and about 5 to 25 weight percent pH-dependent binder, with the remainder being fillers, binders and other optional excipients. A particularly preferred spheroid composition for the administration of nicardipine hydrochloride is:

| Ingredient | Weight % |
| --- | --- |
| Nicardipine HCL | 44.4 |
| Microcrystalline cellulose | 18.5 |
| Lactose | 17.8 |
| Eudragit L100-55 | 18.5 |
| Sodium hydroxide | 0.4 |
| Polyoxyethylene 20 sorbitan mono-oleate | 0.4 |

The coating material may be selected from any conventional enterocoating material which is known to those skilled in the art to which this invention relates. Suitable coating materials include those binder materials listed above. Preferably, both the spheroid partical containing the active ingredient calcium channel blocking agent and the coating provide sustaining action at pH values below about 5.5.

Suitable coating materials include polyvinyl derived polymers and cellulose derived polymers and these may be in the form of organic solvent soluble polymers or aqueous dispersions of the polymers.

Specific suitable polyvinyl derived polymers include the following to name but a few: polyvinyl acetate phthalate (PVAP, Mfr. by Colorcon, pH 4.8, organic solvent soluble); aqueous colloidal dispersion of PVAP (COATERIC-TM, Mfr. by Colorcon, pH 5.0); aqueous dispersion of methacrylic acid methacrylate ester copolymer (Eudragit L, Mfr. by Rohm Pharma, pH 5.5).

Specific suitable cellulose derived polymers include hydroxypropylmethylcellulose phthalate (HPMCP, Mfr. by Shin Etsu, HP-50-TM pH 5 and HP-55 pH 5.5, organic solvent soluble); hydroxypropylmethylcellulose acetate (HPMC-AS-TM, Mfr. by Shin Etsu, pH 5.0 or 5.5, organic solvent soluble;); cellulose acetate trimellitate (CAT-TM, Mfr. by Eastman Kodak, pH 5.5, organic solvent soluble).

A preferred coating suspension for the spheroids is:

| Ingredient | Weight % |
| --- | --- |
| Eudragit L | 12.5 |
| Triethylcitrate | 1.25 |
| Talc | 6.25 |
| Water | 80.0 |

The spheroids are coated with the suspension in a quantity preferably of about 2-20% (solids) of the spheroid weight. A more preferred quantity is 3-10% (solids) of the spheroid weight.

UTILITY AND ADMINISTRATION

Depending on the particular calcium channel blocker which is incorporated, the pharmaceutical compositions and dosage forms of the invention may be used for treating a wide variety of disease states which involve one or more forms of cardiovascular and cerebrovascular disfunction. The calcium channel blockers of interest in the invention generally possess a broad spectrum of cardiovascular and cerebrovascular activities including anti-anginal and antihypertensive properties. Nicardipine also possesses anti-ischemic properties. The invention compositions can therefore be beneficially used in treating cardiovascular and cerebrovascular disorders in patients who are susceptible to calcium ion entry blockade.

The preferred method of administration of these compositions is oral, except in those cases where the patient is unable to ingest, by himself, medication. The preferred oral dosage forms of the invention are capsules, preferably hard gelatin capsules, which contain the long acting spheroids in amounts suitable for the desired dosage period. Other dosage froms for oral administration include powders or spherical particulates for ingestion with foods or beverages.

Because the coated spherical particle compositions of the invention exhibit a prolonged release profile at physiological pH values, they can also be formulated in parenteral suspensions or slow release depot formulations for subcutaneous or intramuscular injection. The parenteral dosage forms can be be prepared by suspending the spheroids and optional pharmaceutical adjuvants in a carrier, such as, for example, water, saline solutions, aqueous dextrose, glycerol and the like. The dosage form may also contain minor but effective amounts of non-toxic auxiliary substances such as wetting and emulsifying agents, pH buffering agents and the like, for example, sodium acetate, sorbitan monolaurate, triethanolamine sodium acetate, triethanolamine oleate and the like. Actual methods of preparing such dosage forms are known, or will be apparent to those skilled in this art; for example, see *Remington's Pharmaceutical Sciences*, Mack Publishing Company, Easton, Pa., 15th Edition, 1975.

The compositions and dosage forms of the present invention provide several therapeutic advantages. Because of the long-acting properties of the coated spheroids, the pharmaceutical compositions and dosage forms of the invention can be designed to provide therapeutic calcium channel blocker plasma concentration profiles suitable for once daily administration. The long acting spheroids may be administered alone or in combination with a conventional powder blend of a calcium channel blocker. In measurements of drug plasma concentration versus time, the improved long acting compositions of the invention provide therapeutic plasma concentrations for a period at least about 24 hours when administered once daily so as to provide substantially the same benefit and advantages afforded by the twice-daily composition according to U.S. Ser. No. 057,469 filed Jul. 26, 1987; now U.S. Pat. No. 4,940,556 without the disadvantages of the instantaneous discharge of high amounts of active ingredient above the amount which can be absorbed before elimination from the patient as is ordinarily observed when administering such high dose of active ingredient.

The following examples are exemplary of the invention described in the specification and claims. They are not to be construed as limiting the scope of the claims.

COMPARISON—EXAMPLE 1

Preparation of Fast Standard Release Powder

A. 2.4 kg nicardipine hydrochloride and 17.5 kg pregelatinized starch were blended for 20 minutes in a Hobart mixer. 0.1 kg of magnesium stearate was then added and blended for 3 minutes.

B. In like manner, fast release powder compositions may be prepared from other dihydropyridine calcium channel blocker including nifedipine, niludipine, nitrendipine, nisoldipine, nimodipine, and felodipine.

COMPARISON—EXAMPLE 2

Preparation of Long Acting Spheroids

A. 1.8 kg of nicardipine hydrochloride, 0.72 kg of microcystalline cellulose and 1.5 kg of Eudragit L100-55 (brand copolymer of methacrylic acid and ethylacrylate) were blended togehter in a Hobart mixer. A solution of 0.03 kg of sodium hydroxide in water was added to the dry mixture and the wet mass was further mixed. The wet mass was extruded through a Nica extruder having a screen size of 0.8 mm and the extrudate was rotated on a Nica spheroniser at about 400 rpm for about 3 minutes. The spheronised particles were then dried in an Aeromatic fluid bed drier at 50° C. for about 120 minutes. The dried spheroids so obtained were sieved and the fraction with diameter greater than 0.71 mm and less than 1 mm was obtained.

B. In like manner, long acting sustained release spheroids may be prepared from other dihydropyridine calcium channel blocker including nifedipine, niludipine, nitrendipine, nisoldipine, nimodipine, and felodipine.

THE INVENTION—EXAMPLE 3

1.8 kg of nicardipine hydrochloride, 0.72 kg of lactose monohydrate, 0.75 kg of microcrystalline cellulose and 0.75 kg of Eudragit L100-55 (brand copolymer of methacrylic acid and ethylacrylate) were blended together in a Hobart mixer. A solution of 0.015 kg of sodium hydroxide and 0.015 kg of polysorbate 20 in water was added to the dry mixture and the wet mass was further mixed. The wet mass was extruded through a Nica extruder having a screen size of 0.8 mm and the extrudate was rotated on a Nica spheroniser at about 400 rpm for about 3 minutes. The spheronized particles were then dried in an Aeromatic fluid bed drier at 50° C. for about 120 minutes. The dried spheroids so obtained were sieved and the fraction with diameter greater than 0.71 mm and less than 1.00 mm was obtained.

405 g of the spheroids were fluidized in an aeromatic fluid bed drier at about 30° C. and a suspension containing 39.06 g of Eudragit L30D (brand copolymer of methacrylic acid and ethylacrylate), 5.859 g of talc and 1.172 g of triethylcitrate in 48 g of water was sprayed onto the spheres. The spheres were then dried at about 50° C. for about 10 minutes and blended with 4.5 g of talc and 0.45 g of colloidal silica.

In a like manner, long acting sustained release spheroids may be prepared from other dihydropyridine calcium channel blockers including nifedipine, niludipine, nitrendipine, nisoldipine, nimodipine and felodipine

EXAMPLE 4

This example shows typical dissolution rates in a standard USP paddle test of a comparison standard release and uncoated long acting nicardipine compositions prepared as described in Examples 1 and 2 in comparison with topical dissolution rates of a coated long acting composition according to this invention prepared as described in Example 3.

The resulting data, set out in Table 1 which follows, whow the necessary additional protection conferred by the coat by virtue of its ability to further reduce the dissolution rate of nicardipine formulation under conditions where the nicardipine shows good solubility. Under these circumstances and at the given dose the high dissolution rates found with the uncoated formulation will manifest themselves as unacceptable high peak plasma levels which are often associated with the onset of unpleasant side effects. These high plasma levels are shown in Example 5 and accompanying Tables 2 and 3.

TABLE 1

| | PERCENT OF NICARDIPINE DISSOLVED | | | | |
|---|---|---|---|---|---|
| | STANDARD RELEASE (20 mg) | UNCOATED LONG-ACTING (120 mg) | | COATED LONG-ACTING (120 mg) | |
| TIME (min) | (a) | (b) | (c) | (b) | (c) |
| 5 | 56 | | | | |
| 10 | 98 | | | | |
| 20 | 99 | | | | |
| 30 | 99 | 29 | 19 | 3 | 17 |
| 60 | 100 | 44 | 42 | 5 | 32 |
| 120 | | 63 | 73 | 9 | 54 |
| 180 | | 76 | 85 | 12 | 68 |
| 240 | | 85 | 90 | 16 | 75 |
| 360 | | 95 | 94 | 22 | 85 |
| 480 | | 101 | 97 | 29 | 91 |
| 720 | | 103 | 97 | 39 | 97 |

(a) Dissolution medium is pH 4.5 citrate buffer
(b) Dissolution medium is 0.1 M hydrochloric acid
(c) Dissolution medium is pH 7.4 phosphate buffer +2% Polysorbate 20*, the brand of polyoxyethylene 20 sorbitan mono-oleate available from Imperial Chemical Industries. A standard USP paddle dissolution test was run at 50 rpm in 1,000 ml of the specified medium.
*Polysorbate 20 is the brand of polyoxyethylene 20 sorbitan mono-oleate supplied by Imperial Chemical Industries.

EXAMPLE 5

In this example the post-administration plasma nicardipine concentrations given by these formulation are compared. The three formulations are (A) a capsule containing uncoated marumes of Example 2;

(B) a capsule containing coated marumes of Example 3; and (C) a capsule containing coated marumes of Example 3 together with standard fast release powder of Example 1.

Plasma samples were withdrawn at intervals and analysed for nicardipine concentration by chromatography. The results are tabulated as measured plasma concentrations and derived pharmacokinetic parameters in Tables 2 and 3 respectively. The results are also shown graphically in FIG. 1 which depicts measured plasma concentrations versus time profiles for formulations A, B and C.

The data shown in FIG. 1 and Tables 2 and 3 demonstrate that while all three formulations are of a sustained release nature, in as much as they give detectable plasma levels 24 hours after dosing, the formulation containing the uncoated product only achieves this at the expense of unacceptably high peak plasma levels e.g., 101.0 ng/ml as compared to 59.2 ng/ml and 60.2 ng/ml for the coated (improved) formulation (Table 2). Tables 2 and 3 and FIG. 1 also clearly indicate that the presence of a fast release loading dose (formulation C) is not required with this improved formulation. Thus only a one component, the coated marumes, capsule fill is necessary which simplifies both processing and subsequent quality control of the product. The improved formulation (formulation B) in addition to having a desirable lower maximum plasma level than the uncoated product also has an equally desirable 70% higher minimum plasma concentration than the uncoated product further indicating the superiority of this improved product for once daily administration.

TABLE 2

NICARDIPINE PLASMA CONCENTRATIONS IN HUMANS (ng/ml)

| TIME POST ADMIN. (H:MIN) | FORMULA-TION A (UNCOATED MARUMES) (90 mg) | FORMULA-TION B (COATED MARUMES) (120 mg) | FORMULATION C (COATED MARUMES 100 mg + standard powder) (20 mg) |
|---|---|---|---|
| 0:00 | 3.36 | 3.02 | 3.54 |
| 0:20 | 3.48 | 3.17 | 3.87 |
| 0:40 | 9.02 | 4.35 | 41.9 |
| 1:00 | 14.0 | 5.45 | 37.9 |
| 1:30 | 11.0 | 7.02 | 29.3 |
| 2:00 | 13.8 | 13.1 | 26.5 |
| 3:00 | 85.2 | 37.5 | 39.9 |
| 4:00 | 101.0 | 52.8 | 57.9 |
| 6:00 | 45.0 | 59.2 | 60.2 |
| 8:00 | 19.6 | 31.2 | 27.6 |
| 10:00 | 10.8 | 14.5 | 18.0 |
| 12:00 | 8.08 | 10.2 | 11.5 |
| 16:00 | 4.74 | 6.10 | 6.94 |
| 20:00 | 3.05 | 3.27 | 3.67 |
| 24:00 | 1.75 | 2.99 | 2.92 |

TABLE 3

DERIVED PHARMACOKINETIC DATA

| | FORMULA-TION A | FORMULA-TION B | FORMULA-TION C |
|---|---|---|---|
| $C_{max}$ (ng/ml) | 106 | 73.8 | 72.6 |
| $C_{24}$ (ng/ml) | 1.75 | 2.99 | 2.92 |
| $T_{max}$ (h) | 3.83 | 4.83 | 5.00 |
| AUC (ng · h/ml) | 472 | 419 | 487 |

*The derived pharmacokinetic parameters were calculated by standard methods well known to anyone experienced in the art (Pharmacokinetics by Gibaldi and Perrier, publisher Marcel Dekker 1975).

The uncoated marumes of U.S. Pat. No. 4,940,556 are well suited for twice-daily administration. However the data here show that administration of uncoated marumes at an increased dose suitable for once-daily administration as indicated by measurable plasma levels at 24 hours after dosing, results in unacceptably high peak plasma levels which range from 43% to 70% higher than the proposed improved formulation. Such higher plasma levels would be more likely to result in higher incidences of side effects. The improved formulation according to the present invention gives a desirable 70% higher plasma level at 24 hours clearly demonstrating its superior sustained release properties for once daily dosing.

These data illustrate the following advantages over the comparison compositions:

(a) Uses no solvents
(b) Readily amenable to large scale production
(c) Most importantly does not rely on a coat only to provide sustained release, i.e., it has a double sustained release action of both coat and marume with rate controlling binder. This reduces the absolute dependency of the integrity of the coat in the prevention of dose dumping resulting in a product which is considerably safer to use.

EXAMPLE 6

Figure 2:
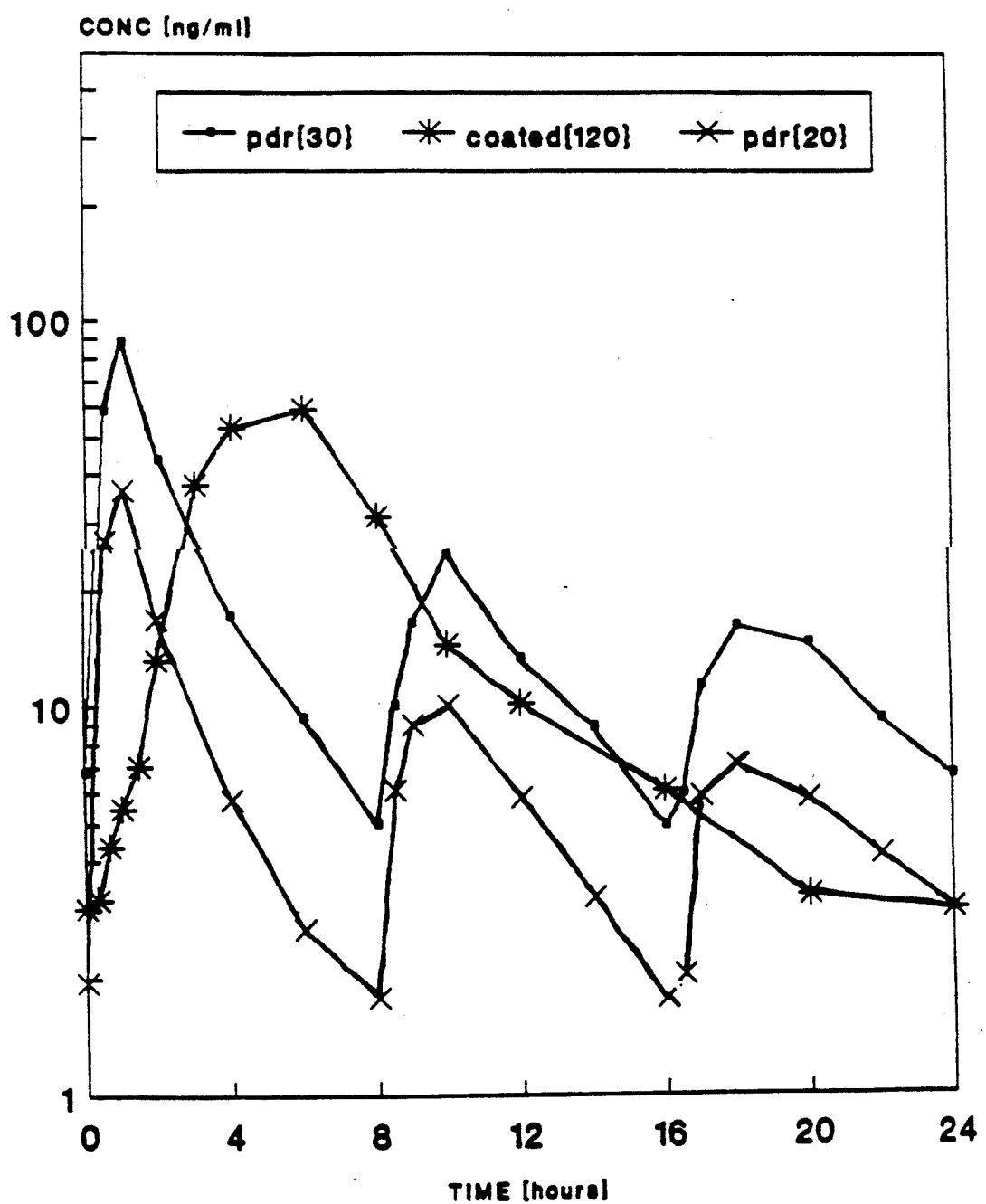
FIG. 2 is a graph showing nicardipine HCl levels over a period of 24 hours for pdr[30], 30 mg fast release powder; coated [120], 120 mg coated marumes; and pdr[20], 20 mg fast release powder.

In this example the typical daily plasma nicardipine concentrations following administration of two formulations are compared. The formulations are two capsules containing 30 mg and 20 mg, respectively, of standard fast release powder ("pdr") of Example 1 given at 8 hourly intervals and a capsule containing 120 mg of coated marumes of Example 3 given at 24 hourly intervals. The results are shown graphically in FIG. 2.

These data demonstrate that once daily administration (administration at 0 hours) of the coated marumes gives maximum plasma concentrations comparable with those given by three daily doses (administered at 0, 8 and 16 hours) of the standard powder, but without the frequent peaks and thoughs associated with the standard powder.

What is claimed is:

1. In an improved long acting sustained release pharmaceutical composition for administration of a therapeutically effective amount of a dihydropyridine calcium channel blocking agent, useful in the treatment of disease conditions that may be alleviated by the administration of calcium channel blocking agents, which comprises essentially spherical, non-coated, non-rugose particles having diameters up to 1.2 millimeter, comprising a therapeutically effective amount of calcium channel blocking agent in intimate admixture with at least about 3 weight percent of a pH-dependent binder, which is less soluble below about pH 4.5 and more soluble above about pH 5.5;

the improvement comprising providing said composition with a single pH-dependent coating applied to said particles containing said calcium channel blocking agent, which is less soluble below about pH 4.5 and more soluble above about pH 5.5, to obtain slow, sustained release of a safe, therapeutically effective amount of the calcium channel blocking agent from said particles over a period of at least about 24 hours.

2. A composition according to claim 1 wherein the dihydropyridine calcium channel blocking agent is a compound selected from the group represented by the formula:

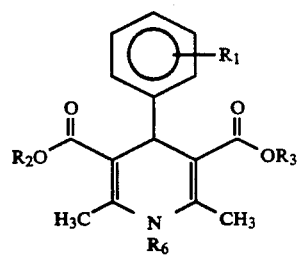

(I)

where;
$R_1$ is —$NO_2$, —$CF_3$, or halo;
$R_2$ is alkyl or —$CH_2CH_2OCH_3$; and
$R_6$ is hydrogen or alkyl; and
$R_3$ is alkyl, alkylenyloxyalkyl, haloalkyl, optionally substituted phenyl alkyl, optionally substituted napthyl alkyl, or

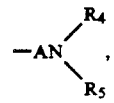

in which:
A is alkylene;

R4 is alkyl, alkoxy, or optionally substituted phenyl or phenyl alkyl; and

R5 is hydrogen or alkyl;

and the pharmaceutically acceptable salts thereof.

3. A composition according to claim 2 wherein
R1 is —NO2,
R2 is CH3,
R3 is

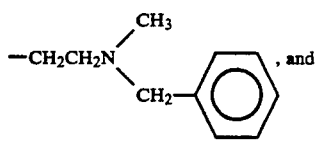, and

R6 is H, and
the hydrochloride salts thereof.

4. A composition according to claim 1 wherein the coating material is selected from polyvinyl polymers and cellulose polymers.

5. A composition according to claim 4 wherein the coating material is a polyvinyl polymer selected from the group of organic solvent soluble polyvinyl acetate phthalate, aqueous dispersions of polyvinyl acetate phthalate and aqueous dispersions of methacrylic acid methacrylate ester copolymer.

6. A composition according to claim 4 wherein the coating material is a cellulose polymer selected from the group of hydroxypropylmethylcellulose phthalate, hydroxypropylmethylcellulose acetate and cellulose acetate trimellitate.

7. An improved long acting sustained release pharmaceutical composition for administration of a therapeutically effective amount of dihydropyridine calcium channel blocking agent, useful in the treatment of disease conditions that may be alleviated by the administration of calcium channel blocking agents, comprising:

essentially spherical, non-coated, non-rugose particles having diameters up to 1.2 millimeter, comprising a therapeutically effective amount of calcium channel blocking agent in intimate admixture with at least about 3 weight percent of a pH-dependent binder, which is less soluble below about pH 4.5 and more soluble above about pH 5.5; and a pH-dependent, outermost coating, that is less soluble below about pH 4.5 and more soluble above about pH 5.5, to obtain slow, sustained release of a safe, therapeutically effective amount of the calcium channel blocking agent over a period of at least about 24 hours, wherein said spherical particles comprise a composition of

| Ingredient | Weight % |
|---|---|
| Nicardipine HCL | 44.4 |
| Microcrystalline cellulose | 18.5 |
| Lactose | 17.8 |
| Methacrylic acid ethylacrylate copolymer | 18.5 |
| Sodium hydroxide | 0.4 |
| Polyoxythylene 20 sorbitan mono-oleate | 0.4 | and wherein the coating is applied to the particles as a suspension comprising

| Ingredient | Weight % |
|---|---|
| Methacrylic acid ethylacrylate copolymer | 12.5 |
| Triethylcitrate | 1.25 |
| Talc | 6.25 |
| Water | 80.0 | the coating suspension being present in an amount sufficient to coat the particles with about 2-20% solids based on the weight of the uncoated particles.

8. A long acting sustained release pharmaceutical composition for administration of a therapeutically effect amount of dihydropyridine calcium channel blocking agent consisting essentially of:

(a) non-rugose, spherical particles, up to 1.2 mm in diameter, comprising the calcium channel blocking agent and a pH-dependent binder; and (b) a pH-dependent, aqueous coating applied to each of said particles, said coating comprising a compound selected from the group consisting of polyvinyl acetate phthalate, methacrylic acid methacrylate ester copolymer, methacrylic acid ethylacrylate copolymer, hydroxypropylmethylcellulose phthalate, hydroxypropylmethylcellulose acetate and cellulose acetate trimellitate;

said pH-dependent binder and said pH-dependent coating being less soluble below about pH 4.5 and more soluble above about pH 5.5.

* * * * *